United States Patent
Rao et al.

(10) Patent No.: US 7,867,758 B2
(45) Date of Patent: Jan. 11, 2011

(54) BIOLUMINOGENIC ASSAY SYSTEM FOR MEASURING BETA-LACTAMASE ACTIVITY

(75) Inventors: Jianghong Rao, Sunnyvale, CA (US); Min-kyung So, Seoul (KR); Hequan Yao, Nanjing (CN)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 457 days.

(21) Appl. No.: 12/060,864

(22) Filed: Apr. 1, 2008

(65) Prior Publication Data

US 2009/0246862 A1 Oct. 1, 2009

(51) Int. Cl.
*C12M 1/00* (2006.01)
*C12Q 1/34* (2006.01)

(52) U.S. Cl. .................. 435/288.7; 435/18; 435/32

(58) Field of Classification Search ................ None
See application file for complete search history.

(56) References Cited

U.S. PATENT DOCUMENTS

| | | |
|---|---|---|
| 5,264,346 A | 11/1993 | Chen |
| 5,338,843 A | 8/1994 | Quante et al. |
| 5,514,561 A | 5/1996 | Quante et al. |
| 5,583,217 A | 12/1996 | Quante et al. |
| 5,741,657 A | 4/1998 | Tsien et al. |
| 5,955,604 A | 9/1999 | Tsien et al. |
| 2007/0020715 A1 * | 1/2007 | Tsien et al. ............ 435/18 |

OTHER PUBLICATIONS

Thomas S. Wehrman, Goerges Von Degenfeld, Peter O Krutzik, Garry P. Nolan, and Helen M. Blau, "Luminescent imaging of β-galactosidase activity in living subjects using sequential reporter-enzyme luminescence", www.nature.com/naturemethods, online Mar. 22, 2006; pp. 295-301, vol. 3 No. 4, Apr. 2006, Nature Publishing Group Sumitaka Hasegawa, Gayatri Gowrishankar, and Jianghong Rao, "Detection of mRNA in Mammalian Cell with a Split Ribozyme Reporter", www.chembiochem.org, published online May 3, 2006; ChemBioChem 2006, 7, pp. 925-928, 2006 Wiley-VCH Verlag GmbH& Co. KGaA, Weinheim.

* cited by examiner

*Primary Examiner*—Herbert J. Lilling
(74) *Attorney, Agent, or Firm*—Mikio Ishimaru

(57) ABSTRACT

A bioluminogenic assay system including: providing a bioluminogenic substrate incorporating a beta-lactam antibiotic, a bioluminescence initiating compound, and a chemical linkage joining the beta-lactam antibiotic to the bioluminescence initiating compound; exposing the bioluminogenic substrate to a beta-lactamase enzyme that catalyzes the release of the bioluminescence initiating compound from the bioluminogenic substrate; co-exposing the bioluminogenic substrate to a bioluminescence indicator reaction that employs the bioluminescence initiating compound as a substrate; and detecting a light from the bioluminescence indicator reaction as a measure of the activity of the beta-lactamase enzyme.

18 Claims, 6 Drawing Sheets

BIOLUMINOGENIC ASSAY SYSTEM FOR MEASURING BETA-LACTAMASE ACTIVITY

FEDERALLY-SPONSORED RESEARCH OR DEVELOPMENT

This invention was made with Government support under contract EB003803awarded by the National Institutes of Health. The Government has certain rights in this invention.

TECHNICAL FIELD

The present invention relates generally to enzyme chemistry, and more particularly to a bioluminogenic system for assaying beta-lactamase activity.

BACKGROUND ART

Patients can die when bacteria enters the blood stream, a condition known bacteremia. This condition may occur as a result of a wound or infection, or through an invasive procedure such as surgery or an injection. Treatment of bacteremia requires hospitalization and includes the administration of intraveneous antibiotics. A life-threatening condition may develop if the bacteria are immune or resistant to the antibiotic regime used for treatment.

Once a bacterial infection reaches the blood stream, doctors only have up to 6 to 12 hours to treat the infection with the correct antibiotic before the infection will kill the patient. In those situations, understanding whether the bacteria in question is resistant to an antibiotic is critical to selecting the appropriate treatment that can save the patient. Bacterial resistance or immunity to antibiotics is becoming a growing global health problem.

In order to understand how bacterial resistance occurs, it is necessary to understand enzymes, which are complex proteins produced by living cells that speed-up or accelerate specific biochemical reactions. Enzymes are found in bacteria and it has been discovered that bacteria making, or expressing, enzymes called beta-lactamases ($\beta$-lactamases) are immune or resistant to $\beta$-lactam antibiotics.

This resistance occurs because these enzymes efficiently open up, or hydrolyze, $\beta$-lactam 4-atom rings found in major antibiotics such as penicillins, cephamycins, cephalosporins, and carbapenemes. This modification of the antibiotic molecule significantly reduces or eliminates its effectiveness as a treatment for the bacterial infection.

As a result, the ability to rapidly and accurately determine the existence of $\beta$-lactamase enzymes inside the disease causing bacteria will allow a doctor to provide an appropriate treatment that does not include beta-lactam antibiotics, and thus increase the effectiveness of the treatment and reduce potential adverse reactions from enzyme-modified beta-lactam antibiotics.

While a number of calorimetric and fluorometric compounds have been developed for the detection of $\beta$-lactamase outside the living body in a laboratory environment (in vitro), use of these compounds require external light sources to measure the presence of the enzyme. These techniques are more difficult or not possible to implement inside living creatures because the light may not reach deep tissues due to absorption of proteins such as hemoglobin, or it may generate artifacts, for example auto-fluorescence from native proteins, that may interfere with the measurement.

Detection of $\beta$-lactamases is also important to the study of biological processes, a scientific activity that is necessary to understand diseases and in developing cures. One application is the use of $\beta$-lactamase detection as a signal that a given biological process is taking place inside a living cell. A reporter system is a gene that, when it is incorporated ("transfected") into a cell, is transformed into a protein that can be readily detected. For example, TEM-1 $\beta$-lactamase (Bla), a small (29 kDa) and monomeric enzyme, is a sensitive reporter system for detecting and for creating a spatial image of biological processes and interactions in single living cells and in tissue extracts or cultures.

Thus, a need still remains for a compound for measuring beta-lactamase enzymes that can be used inside living creatures (in vivo experiments). In addition, it would be desirable to locate exactly where the beta-lactam bacterial infection is occurring in the body by creating a spatial image showing beta-lactamase enzyme levels.

In addition, there is a need to improve the sensitivity and ease-of-use of reporter systems used for scientific research and drug development. Assay improvements generally enable new applications and reduce the cost of research and development of new pharmaceuticals or biotechnology products.

In view of the clinical importance of bacterial resistance to antibiotics, it is increasingly critical that answers be found to these problems.

Solutions to these problems have been long sought but prior developments have not taught or suggested any solutions and, thus, solutions to these problems have long eluded those skilled in the art.

DISCLOSURE OF THE INVENTION

The present invention provides a bioluminogenic assay system including: providing a bioluminogenic substrate incorporating a beta-lactam antibiotic, a bioluminescence initiating compound, and a chemical linkage joining the beta-lactam antibiotic to the bioluminescence initiating compound; exposing the bioluminogenic substrate to a beta-lactamase enzyme that catalyzes the release of the bioluminescence initiating compound from the bioluminogenic substrate; co-exposing the bioluminogenic substrate to a bioluminescence indicator reaction that employs the bioluminescence initiating compound as a substrate; and detecting a light from the bioluminescence indicator reaction as a measure of the activity of the beta-lactamase enzyme.

Certain embodiments of the invention have other aspects in addition to or in place of those mentioned above. The aspects will become apparent to those skilled in the art from a reading of the following detailed description when taken with reference to the accompanying drawings.

BEST MODE FOR CARRYING OUT THE INVENTION

Figure 1:
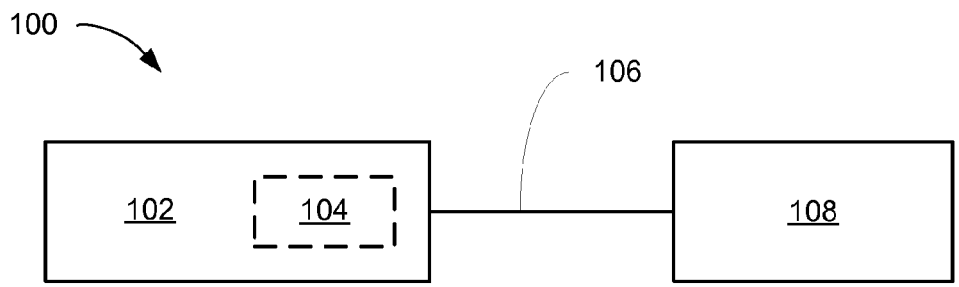
FIG. 1 is a conceptual diagram of the chemical structure of a bioluminogenic substrate used for the bioluminogenic assay system of the present invention.

The following embodiments are described in sufficient detail to enable those skilled in the art to make and use the invention. It is to be understood that other embodiments would be evident based on the present disclosure, and that system, process, or chemical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known process steps are not disclosed in detail. Likewise, the drawings showing embodiments of the system are semi-diagrammatic and not to scale and, particularly, some of the dimensions are for the clarity of presentation and are shown greatly exaggerated in the drawing FIGs. In addition, where multiple embodiments are disclosed and described having some features in common, for clarity and ease of illustration, description, and comprehension thereof, similar and like features one to another will ordinarily be described with like reference numerals. The term "system" as used herein refers to and is defined as the method and as the apparatus of the present invention in accordance with the context in which the term is used.

Referring now to FIG. 1, therein is shown a conceptual diagram of the chemical structure of a bioluminogenic substrate 100 used for the bioluminogenic assay system of the present invention. The bioluminogenic substrate contains three main elements, a beta-lactam antibiotic 102 with a beta-lactam ring 104 incorporated within its chemical structure, a chemical linkage 106, and a bioluminescence initiating compound 108.

The term "beta-lactam antibiotic" as used herein is defined as an antibiotic agent that contains the beta-lactam ring 104 within its molecular structure. The term "chemical linkage" as used herein is defined as a molecule or element linking two molecules, and may include covalent, hydrogen, or ionic chemical bonds. The term "bioluminescence initiating compound" as used herein is defined as any chemical compound that results in the generation of bioluminescence when combined with a bioluminescent enzyme.

Examples of the bioluminescence initiating compound 108 include, but are not limited to, luciferin and coelenterazine and their analogs thereof and their functional derivatives thereof. Derivatives of coelenterazine include, but are not limited to, coelenterazine 400a, coelenterazine cp, coelenterazine f, coelenterazine fcp, coelenterazine h, coelenterazine hep; coelenterazine ip, coelenterazine n, coelenterazine O, coelenterazine c, coelenterazine i, coelenterazine icp, coelenterazine 2-methyl, benzyl-coelenterazine bisdeoxycoelenterazine, and deep blue coelenterazine (DBC).

EXAMPLE 1

Bioluminogenic Substrate System Employing Cephalosporin and D-luciferin

Figure 2:
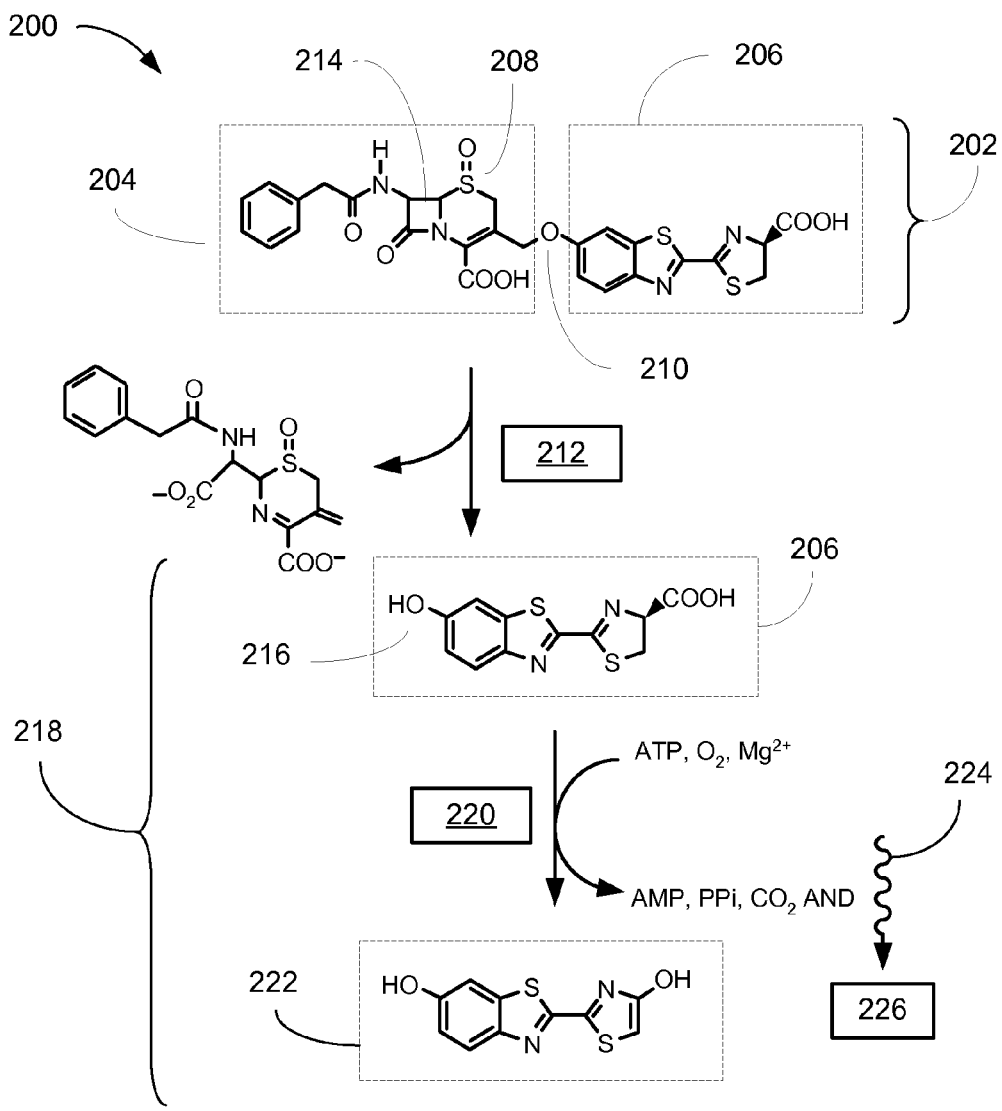
FIG. 2 is a bioluminogenic assay system for the detection of beta-lactamase activity in one embodiment of the present invention.

Referring now to FIG. 2, therein is shown a bioluminogenic assay system 200 for the detection of beta-lactamase activity in one embodiment of the present invention. As one embodiment of the bioluminogenic substrate 100 shown in FIG. 1, a bioluminogenic substrate 202 incorporates a cephalosporin molecule 204 as the beta-lactam antibiotic 102 shown in FIG. 1, and a D-luciferin molecule 206 as the bioluminescence initiating compound 108 depicted in FIG. 1. In this embodiment of the invention the sulfide group in the cephalosporin molecule 204 is oxidized to a sulfoxide functionality 208 to improve the stability of the bioluminogenic substrate 202. The chemical linkage 106 shown schematically in FIG. 1 is implemented by coupling the 3' position of the cephalosporin molecule 204 to the 6-hydroxy group of the D-luciferin molecule through an ether bond 210.

In the first step of the two-step reaction used for the bioluminogenic assay system 200, a beta-lactamase enzyme 212 catalyzes the opening of a beta-lactam ring 214 in the cephalosporin molecule 204. The opening of a beta-lactam ring 214 in the cephalosporin molecule 204 triggers spontaneous fragmentation, leading to the cleavage of the ether bond 210 between the cephalosporin molecule 204 and the D-luciferin molecule 206. This cleavage of the ether bond 210 releases the D-luciferin molecule 206 and restores a 6-hydroxy group 216 to the D-luciferin molecule 206.

Once released from the bioluminogenic substrate 202, the D-luciferin molecule 206 becomes a substrate for a bioluminescence indicator reaction 218 catalyzed by a firefly luciferase enzyme 220. Conversely, the bioluminogenic substrate 202 incorporating the D-luciferin molecule 206 is not a suitable substrate for the bioluminescence indicator reaction 218 catalyzed by the firefly luciferase enzyme 220.

In the bioluminescence indicator reaction 218, the firefly luciferase enzyme 220 catalyzes the oxidation of the D-luciferin molecule 206 in the presence of oxygen ($O_2$), adenosine triphosphate (ATP), and magnesium ion ($Mg^{2+}$), forming an oxyluciferin molecule 222, adenosine monophosphate (AMP), pyrophosphates ($PP_i$), carbon dioxide ($CO_2$), and a light emission 224. The light emission 224 generated by the bioluminescence indicator reaction 218 is directly detectable by an optoelectronic sensor 226 such as a photomultiplier tube, photodiode, Geiger-mode photodiode, CCD detector, or a CMOS array detector, and provides a signal representative of the activity of the beta-lactamase enzyme 212.

Figure 3:
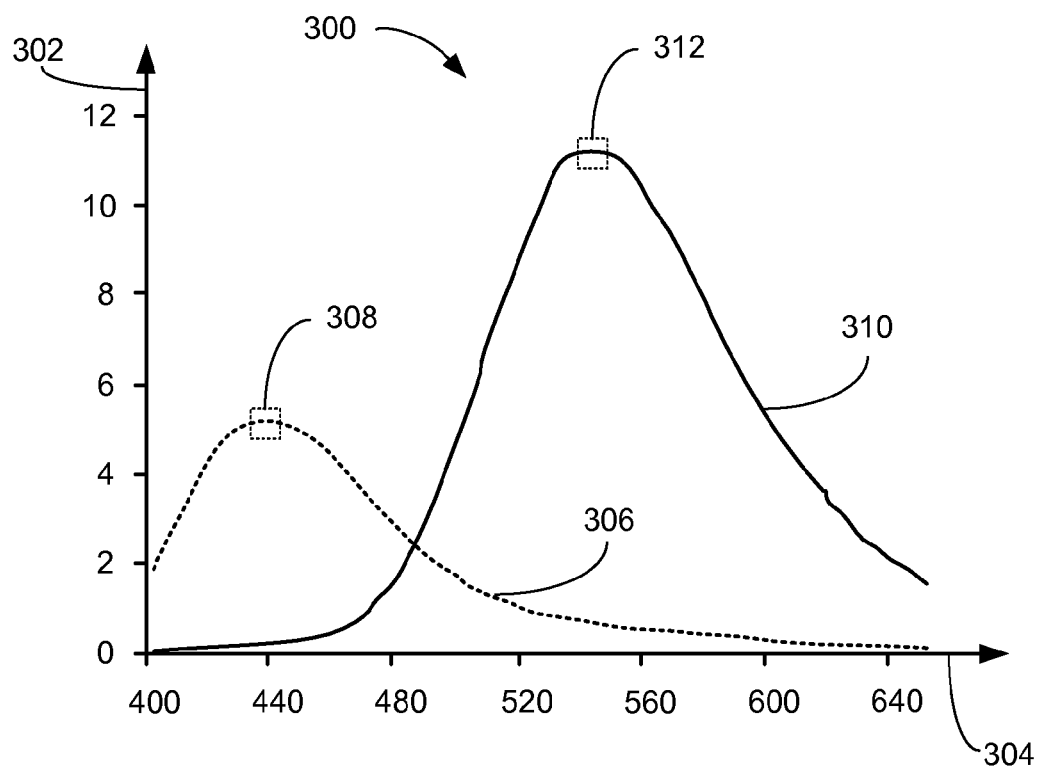
FIG. 3 is a fluorescence emission spectra of the bioluminogenic substrate of FIG. 2 before and after exposure to the beta-lactamase enzyme.

Referring now to FIG. 3, therein is shown a fluorescence emission spectra 300 of the bioluminogenic substrate 202 of FIG. 2 before and after exposure to the beta-lactamase enzyme 212. In this study, 10 µM of the bioluminogenic substrate 202 was diluted in 10 mM PBS buffer. The excitation wavelength used to measure the emission spectra was 350 nm. The fluorescence emission spectra 300 are determined by a fluorescence signal 302 (in millions of relative fluorescence units) measured as a function of emission wavelength 304 (in nm).

A fluorescence signal 306 in FIG. 3 shows the emission spectrum of the bioluminogenic substrate 202 (FIG. 2). As shown by the fluorescence signal 306, the bioluminogenic substrate 202 has a maximal emission peak 308 at 440 nm. A fluorescence signal 310 in FIG. 3 shows the emission spectrum of the bioluminogenic substrate 202 (FIG. 2) after treatment with the beta-lactamase enzyme 212. The fluorescence signal 308, as a result of the treatment with the beta-lactamase enzyme 212, is red-shifted, showing a maximal emission peak 312 at 560 nm.

The fluorescence emission spectra 300 shown in FIG. 3 illustrate the fact that the bioluminogenic substrate 202 may also be employed as a fluorogenic substrate. However, it is expected that use of the bioluminogenic assay system 200 shown in FIG. 2 produces a signal with a significantly better signal-to-noise ratio than use of the bioluminogenic substrate 202 as a fluorogenic substrate as shown by the emission spectra shown in FIG. 3. Moreover, hemoglobin absorption precludes using the bioluminogenic substrate 202 as a fluorogenic substrate, since excitation at 350 nm has a very low penetration depth in an in vivo system.

Figure 4:
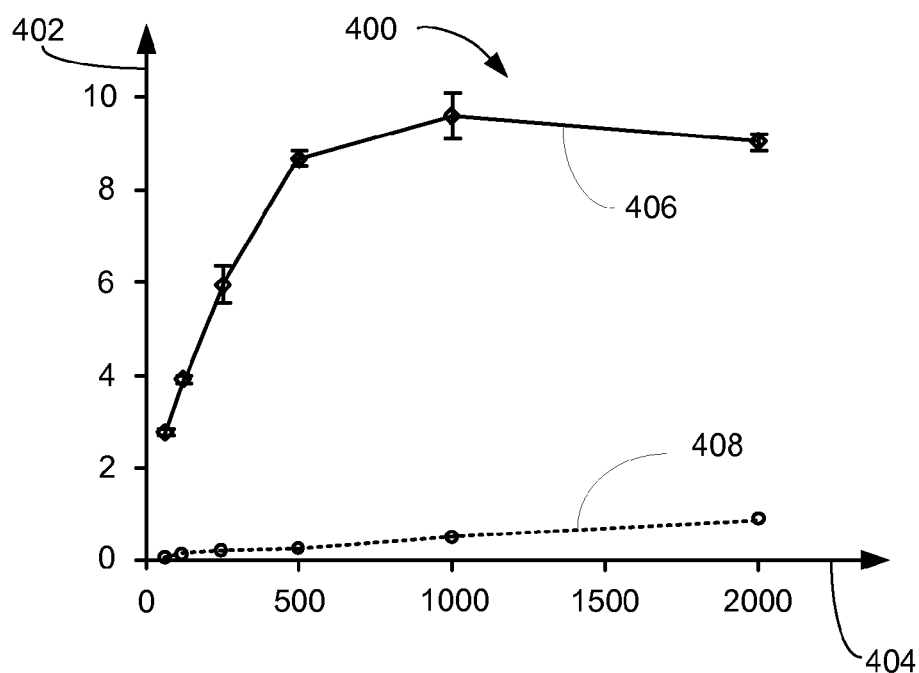
FIG. 4 is a plot showing the bioluminescence emission from intact COS7 (monkey kidney cells) transfected with both beta-lactamase and firefly luciferase (Bla+fluc) or only firefly luciferase (fluc)

Referring now to FIG. 4, therein is shown a plot 400 showing the bioluminescence emission from intact COS7 (monkey kidney cells) transfected with both beta-lactamase and firefly luciferase (Bla+fluc) or only firefly luciferase (fluc). The bioluminescence emission measurement is performed using $1 \times 10^5$ intact COS7 cells in each case, following a 10-minute incubation with different concentrations of the bioluminogenic substrate 202. The plot 400 shows a bioluminescence signal 402 in increments of 105 relative luminescence units (RLUs) as a function of a concentration 404 of the bioluminogenic substrate 202 in μM units. A signal 406 is the bioluminescence emission from COS7 cells transfected with both beta-lactamase and firefly luciferase and a control signal 408 is the bioluminescence emission from COS7 cells transfected with firefly luciferase alone.

The data shown in the plot 400 in FIG. 4 illustrates that the contrast between the signal 406 (representing the bioluminescence from the COS7 cells transfected with Bla+fluc) and the control signal 408 (representing the bioluminescence from the COS7 cells transfected with fluc alone) is more than 55-fold. The signal 406 appears to saturate when the bioluminogenic substrate 202 concentration exceeds 500 μM.

Figure 5:
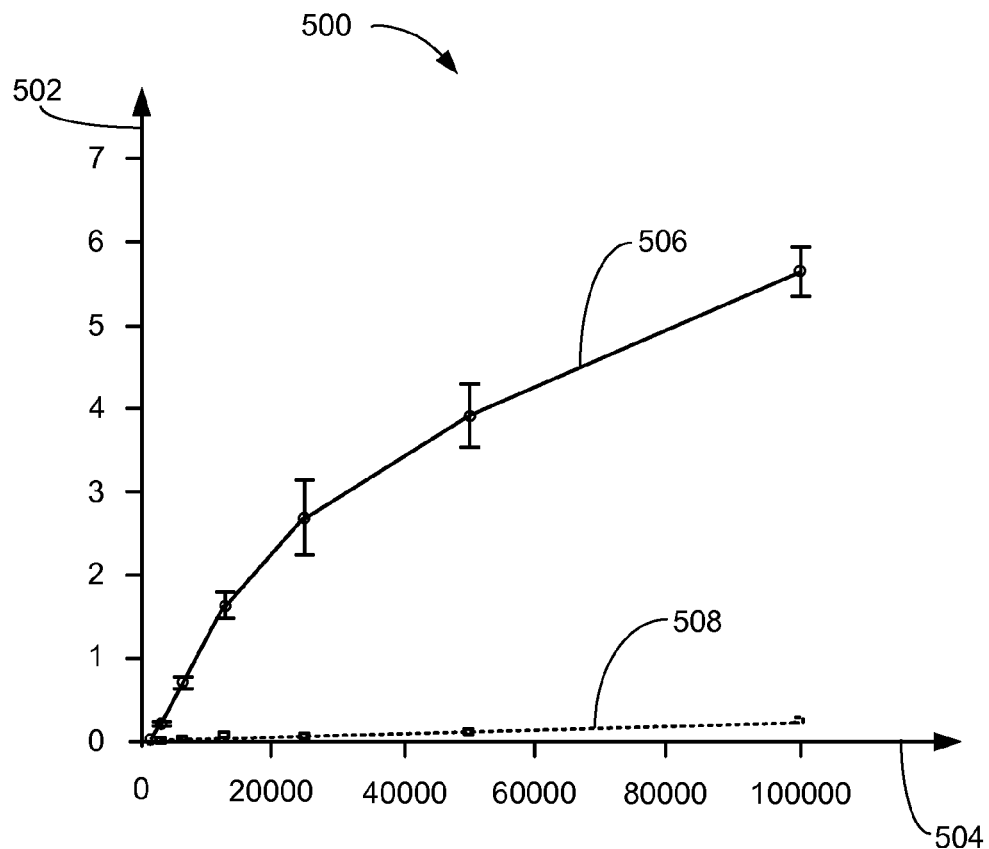
FIG. 5 a plot showing bioluminescence emission from COS7 (monkey kidney cells) transfected with both beta-lactamase and firefly luciferase (Bla+fluc) or only firefly luciferase (fluc)

Referring now to FIG. 5, therein is shown a plot 500 showing bioluminescence emission from COS7 (monkey kidney cells) transfected with both beta-lactamase and firefly luciferase (Bla+fluc) or only firefly luciferase (fluc). The bioluminescence emission measurement is performed following a 10-minute incubation with 500 μM of the bioluminogenic substrate 202 of FIG. 2. The plot 500 shows a bioluminescence signal 502 in increments of 105 relative luminescence units (RLUs) as a function of a cell number 504. A signal 506 is the bioluminescence emission from COS7 cells transfected with both beta-lactamase and firefly luciferase and a control signal 508 is the bioluminescence emission from COS7 cells transfected only with firefly luciferase alone.

As shown in the plot 500 in FIG. 5 the signal 506 increases monotonically with cell number. As few as 1500 intact COS7 cells are detected in the presence of 500 μM of the bioluminogenic substrate 202. The data shown in the plot 400 in FIG. 4 and the plot 500 in FIG. 5 demonstrate that the bioluminogenic substrate 202 is a cell-permeable detector for the beta-lactamase enzyme 212 in mammalian cells.

Figure 6:
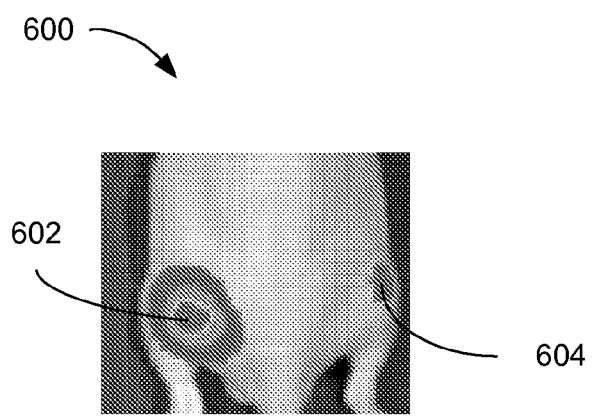
FIG. 6 is a tracing of an image showing beta-lactamase activity in a living nude mouse.

Referring now to FIG. 6, therein is shown an image 600 showing beta-lactamase activity in a living nude mouse. The mouse received an injection with $1 \times 10^6$ COS7 cells co-transfected with beta-lactamase and firefly luciferase (Bla+fluc) into the left rear tight, and a second injection with 1×106 COS7 cells transfected with firefly luciferase (fluc) into the right rear tight. Two hours after cell implantation, 78 mg of the bioluminogenic substrate 202 is injected intravenously into the tail vein of the mouse. A first bioluminescence signal 602 measured in units of photons per cm2 per steredian is registered over the left tight area. A second bioluminescence signal 604 measured in units of photons per cm2 per steredian is measured over the left tight area. The first bioluminescence signal 602 is 15 to 25 fold more intense than the second bioluminescence signal 604, demonstrating the contrast provided by the bioluminogenic assay system 200 in an in vivo environment.

EXAMPLE 2

Detection and Imaging of the Tetrahymena Ribozyme-splicing

Figure 7:
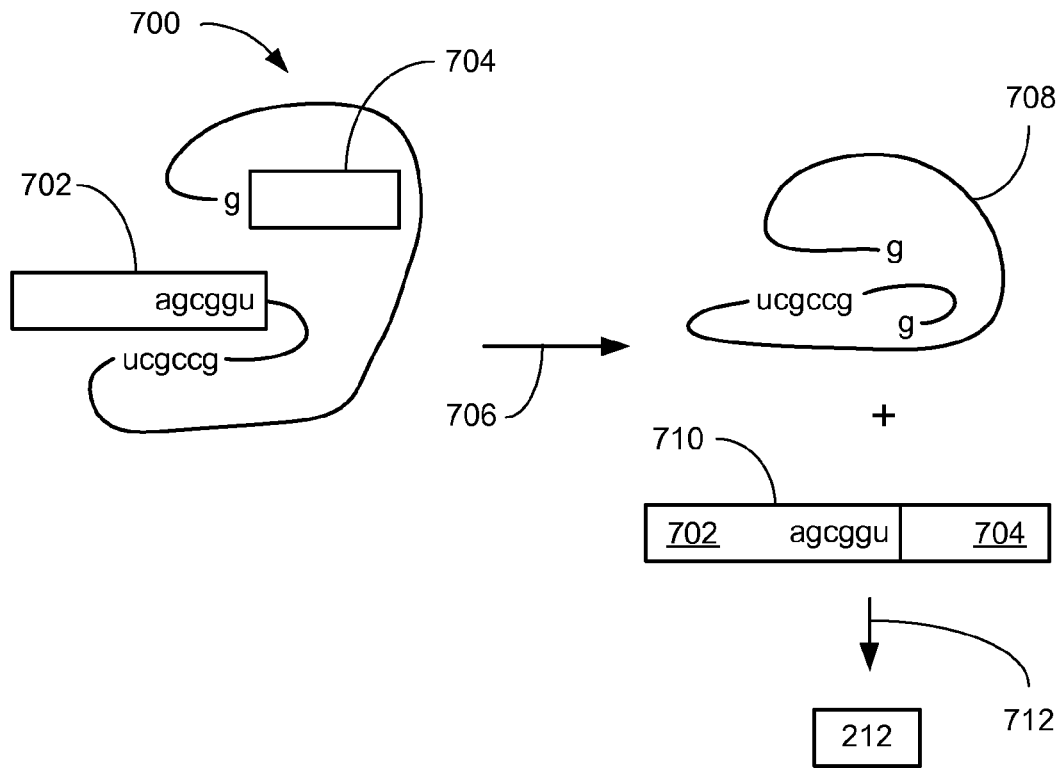
FIG. 7 is a schematic diagram illustrating a Tetrahymena ribozyme reporter incorporating RNA fragments encoding the beta-lactamase enzyme.

Referring now to FIG. 7, therein is shown a schematic diagram illustrating a Tetrahymena ribozyme reporter 700 incorporating RNA fragments encoding the beta-lactamase enzyme 212. The Tetrahymena ribozyme reporter 700 incorporates a RNA fragment-I 702 encoding part of the beta-lactamase enzyme 212 and a RNA fragment-II 704 encoding the remaining part of the beta-lactamase enzyme 212. The Tetrahymena ribozyme reporter 700 is transfected into COS7 cells. A splicing process 706 joins the RNA fragment-I 702 to the RNA fragment-II 706, creating a complete RNA construct 710 encoding the beta-lactamase enzyme 212, and a ribozyme structure 708. Subsequently, a translation process 712 within the COS7 cells creates expression of the beta-lactamase enzyme 212 within the COS7 cells.

Figure 8:
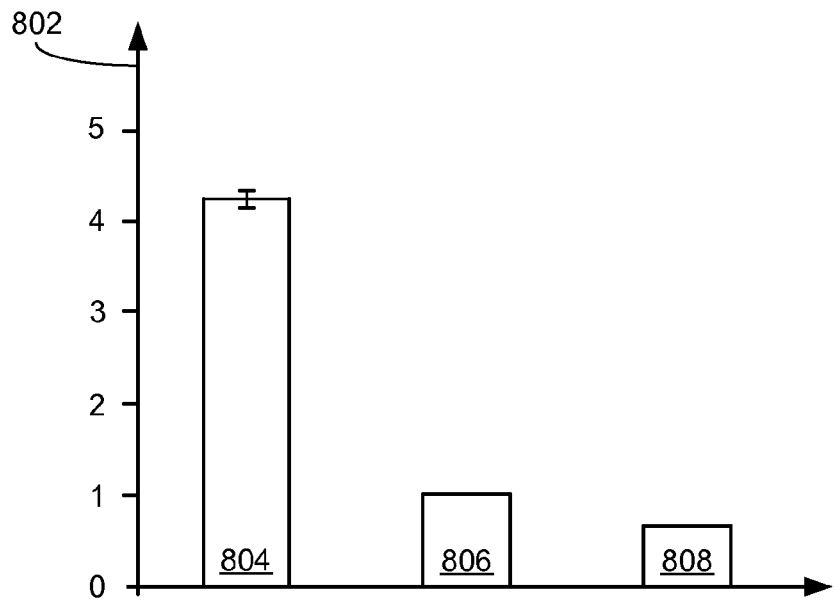
FIG. 8 a plot showing the bioluminescence emission from intact COS7 cells transfected with ribozyme constructs in combination with firefly luciferase or transfected with firefly luciferase alone.

Referring now to FIG. 8, therein is shown a plot 800 showing the bioluminescence emission from intact COS7 cells transfected with ribozyme constructs in combination with firefly luciferase, or transfected with firefly luciferase alone. The bioluminescence emission measurement is performed using $1 \times 10^5$ intact COS7 cells transfected with both the Tetrahymena ribozyme reporter 700 and firefly luciferase (RzB+ fluc), transfected with an inactive mutant of the Tetrahymena ribozyme reporter 700 and firefly luciferase (RzBm+fluc), or transfected only with firefly luciferase (fluc) following a 30 minute incubation 500 μM of the bioluminogenic substrate 202.

The plot 800 shows a bioluminescence signal 802 in increments of 104 relative luminescence units (RLUs) for a RzB+ fluc reporter 804, a RzBm+fluc reporter 806, and an fluc reporter 808. As it can be seen in the plot 800, the signal for the RzB+fluc reporter 804 is four times higher than the signal for the RzBm+fluc reporter 806 or the fluc reporter 808. The RzBm+fluc reporter 806 incorporates an inactive mutant of the Tetrahymena ribozyme reporter 700 (RzBm) with a single mutation at the catalytic site.

EXAMPLE 3

Use of Coelenterazine or it Derivatives for the Bioluminogenic Substrate

Figure 9:
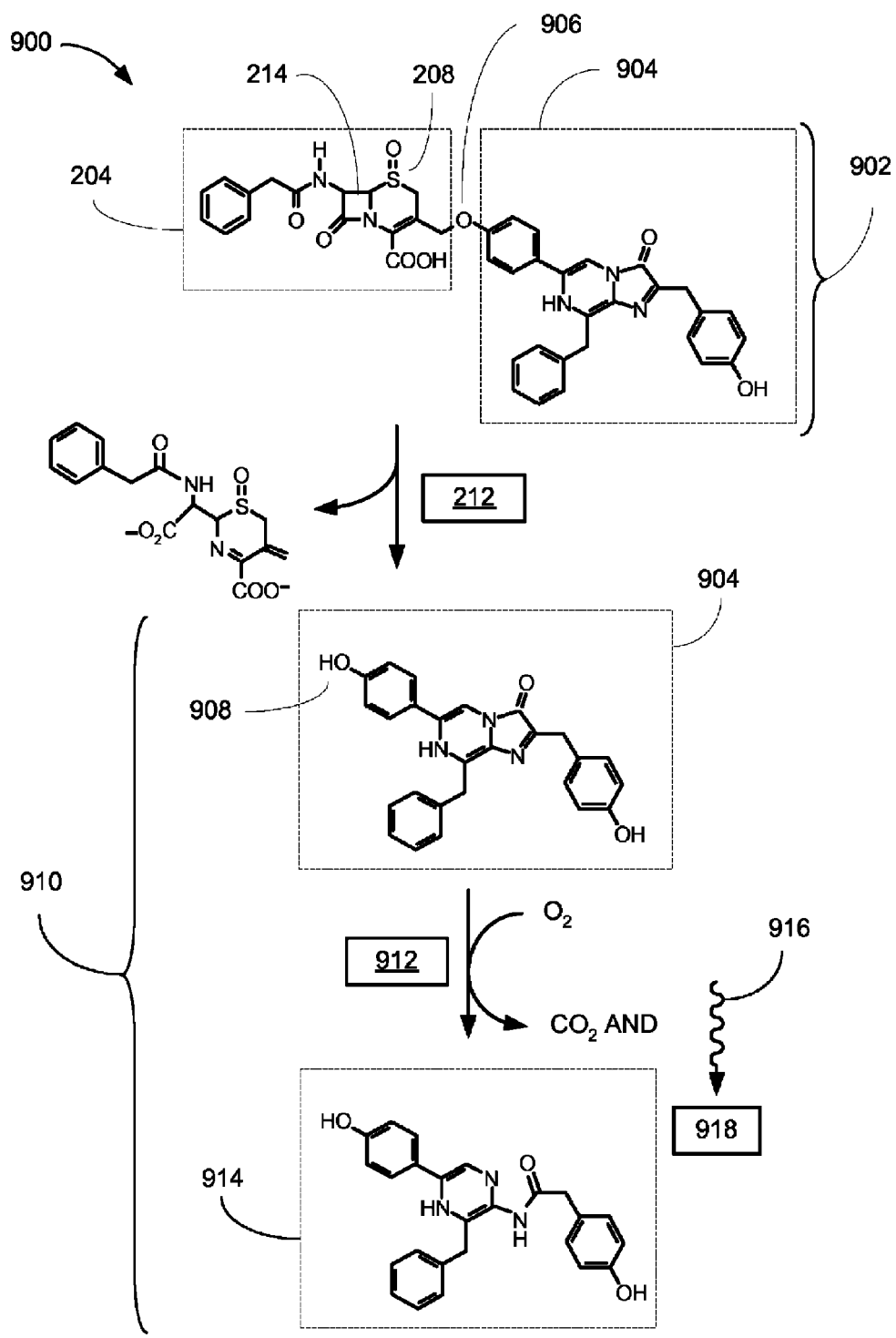
FIG. 9 is a bioluminogenic assay system for the detection of beta-lactamase activity in one embodiment of the present invention.

Referring now to FIG. 9, therein is shown a bioluminogenic assay system 900 for the detection of beta-lactamase activity in one embodiment of the present invention. A bioluminogenic substrate 902 incorporates the cephalosporin molecule 204 as the beta-lactam antibiotic 102 shown in FIG. 1, and a coelenterazine molecule 904 as the bioluminescence initiating compound 108 depicted in FIG. 1. In this embodiment of the invention the sulfide group in the cephalosporin molecule 204 is oxidized to the sulfoxide functionality 208 to improve the stability of the bioluminogenic substrate 902. The chemical linkage 106 shown schematically in FIG. 1 is implemented by coupling the 3' position of the cephalosporin molecule 204 to the 6-hydroxy group of the coelenterazine molecule 904 through an ether bond 906.

In the first step of the two-step reaction used for the bioluminogenic assay system 900, the beta-lactamase enzyme 212 catalyzes the opening of the beta-lactam ring 214 in the cephalosporin molecule 204. The opening of the beta-lactam ring 214 in the cephalosporin molecule 204 triggers spontaneous fragmentation, leading to the cleavage of the ether bond 906 between the cephalosporin molecule 204 and the coelenterazine molecule 904. This cleavage of the ether bond 906 releases the coelenterazine molecule 904 and restores a 6-hydroxy group 908 to the coelenterazine molecule 904.

Once released from the bioluminogenic substrate 902, the coelenterazine molecule 904 becomes a substrate for a bioluminescence indicator reaction 910 catalyzed by a *Renilla* luciferase enzyme 912. Conversely, the bioluminogenic substrate 902 incorporating the coelenterazine molecule 904 is not a suitable substrate for the bioluminescence indicator reaction 910 catalyzed by the *Renilla* luciferase enzyme 912. Gaussia luciferase or any other bioluminescence enzyme that employs coelenterazine or its derivatives as a substrate can be used as a substitute for the *Renilla* luciferase enzyme 912.

In the indicator reaction, the *Renilla* luciferase enzyme 912 catalyzes the reaction of the coelenterazine molecule 904 with oxygen ($O_2$), forming a coelenteramide molecule 914, carbon dioxide ($CO_2$), and a light emission 916. The light emission 916 generated by the indicator reaction is directly detectable by an optoelectronic sensor 918 such as a photomultiplier tube, photodiode, Geiger-mode photodiode, CCD detector, or a CMOS array detector, and provides a signal representative of the activity of the beta-lactamase enzyme 212.

Figure 10:
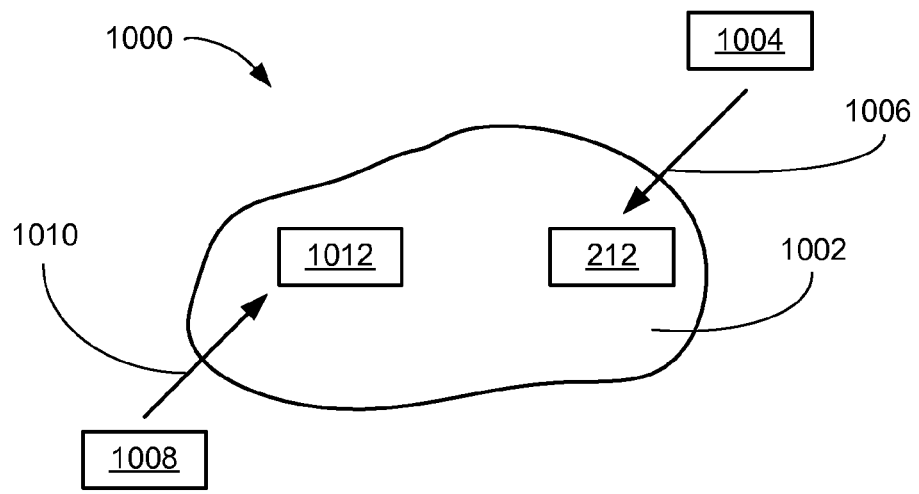
FIG. 10 is a schematic diagram showing a reporter system for the beta-lactamase enzyme 212 and a bioluminescence enzyme.

Referring now to FIG. 10, therein is shown a schematic diagram showing a reporter system 1000 for the beta-lactamase enzyme 212 and a bioluminescence enzyme 1012. The reporter system 1000 is one means for implementing assay 200 of FIG. 2 or assay 900 of FIG. 9 inside a biological cell 1002. In one embodiment of the invention the reporter system involves performing a first transfection 1006 of a beta-lactamase vector 1002 that results in the expression of the beta-lactamase enzyme 212, and a second transfection 1010 of a bioluminescence enzyme vector 1008 that results in the expression of a bioluminescence enzyme 1012. Examples of the bioluminescence enzyme include the firefly luciferase enzyme 220 and the *Renilla* luciferase enzyme 912. The beta-lactamase vector 1002 and the bioluminescence enzyme 1012 vector may be co-transfected using a single plasmid.

Figure 11:
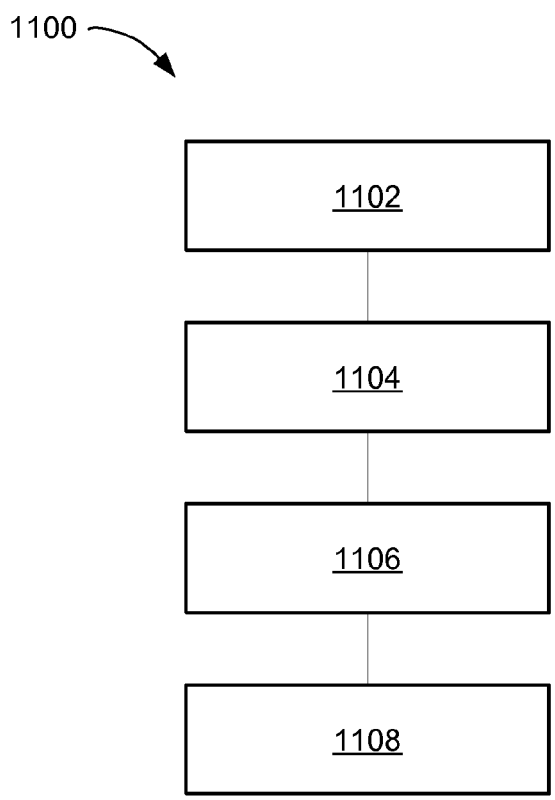
FIG. 11 is a flow chart of a system for a bioluminogenic assay system for measuring beta-lactamase activity in an embodiment of the present invention.

Referring now to FIG. 11, therein is shown a flow chart of a system 1100 for a bioluminogenic assay system for measuring beta-lactamase activity in an embodiment of the present invention. The system 1100 includes providing a bioluminogenic substrate incorporating a beta-lactam antibiotic, a bioluminescence initiating compound, and a chemical linkage joining the beta-lactam antibiotic to the bioluminescence initiating compound in a block 1102; exposing the bioluminogenic substrate to a beta-lactamase enzyme that that catalyzes the release of the bioluminescence initiating compound from the bioluminogenic substrate in a block 1104; co-exposing the bioluminogenic substrate to a bioluminescence indicator reaction that employs the bioluminescence initiating compound as a substrate in a block 1106; and detecting the light output from the bioluminescence indicator reaction as a measure of the activity of the beta-lactamase enzyme in a block 11108.

It has been discovered that the present invention thus has numerous aspects.

A principle aspect that has been unexpectedly discovered is that the present invention provides a convenient and sensitive beta-lactamase reporter system compatible with both in vitro and in vivo environments.

Another important aspect of the invention is that the bioluminescence assay system can be implemented using bioluminescence enzymes that employ coelenterazine as a bioluminescence initiating compound, such as *Renilla* luciferase and Gaussia luciferase.

Another important aspect of the invention is that the inventive bioluminogenic substrate used for the bioluminogenic assay system is permeable through cell membranes.

Yet another important aspect of the present invention is that it valuably supports and services the historical trend of reducing costs, simplifying systems, and increasing performance.

These and other valuable aspects of the present invention consequently further the state of the technology to at least the next level.

Thus, it has been discovered that the bioluminescence assay system of the present invention furnishes important and heretofore unknown and unavailable solutions, capabilities, and functional aspects for measuring the activity of beta-lactamase and for use as a reporter system. The resulting processes and configurations are straightforward, cost-effective, uncomplicated, highly versatile, accurate, sensitive, and effective, and can be implemented by adapting known components for ready, efficient, and economical manufacturing, application, and utilization.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A bioluminogenic assay system comprising:
   providing a bioluminogenic substrate incorporating a beta-lactam antibiotic, a bioluminescence initiating compound, and an ether bond joining the beta-lactam antibiotic to the bioluminescence initiating compound, the bioluminescence initiating compound being selected from a D-luciferin molecule, a coelenterazine molecule, and their derivatives and analogs;
   exposing the bioluminogenic substrate to a beta-lactamase enzyme that catalyzes the release of the bioluminescence initiating compound from the bioluminogenic substrate;
   co-exposing the bioluminogenic substrate to a bioluminescence indicator reaction catalyzed by a bioluminescent enzyme that employs the bioluminescence initiating compound as a substrate; and
   detecting a light from the bioluminescence indicator reaction using an optoelectronic sensor as a measure of the activity of the beta-lactamase enzyme.

2. The bioluminogenic assay system as claimed in claim 1 wherein exposing the bioluminogenics substrate to a beta-lactamase enzyme is performed using a beta-lactamase vector transfected into a biological cell.

3. The bioluminogenic assay system as claimed in claim 1 wherein co-exposing the bioluminogenic substrate to a bioluminescence indicator reaction is performed using a bioluminescence enzyme vector transfected into a biological cell.

4. The bioluminogenic assay system as claimed in claim 1 wherein the bioluminogenic assay system is performed in vivo.

5. The bioluminogenic assay system as claimed in claim 1 wherein the beta-lactamase enzyme is provided within a biological specimen.

6. A bioluminogenic assay system comprising:
providing a bioluminogenic substrate incorporating a cephalosporin molecule, a bioluminescence initiating compound, and an ether bond linking the cephalosporin molecule to the bioluminescence initiating compound, the bioluminescence initiating compound being selected from a D-luciferin molecule, a coeienterazine molecule, and their derivatives and analogs;
exposing the bioluminogenic substrate to a beta-lactamase enzyme that catalyzes the release of the bioluminescence initiating compound from the bioluminogenic substrate;
co-exposing the bioluminogenic substrate to a bioluminescence indicator reaction catalyzed by a bioluminescent enzyme that employs the bioluminescence initiating compound as a substrate; and
detecting the light from the bioluminescence indicator reaction using an optoelectronic sensor as a measure of the activity of the beta-lactamase enzyme.

7. The bioluminogenic assay system as claimed in claim 6 wherein exposing the bioluminogenics substrate to a beta-lactamase enzyme is performed using a beta-lactamase vector transfected into a biological cell.

8. The bioluminogenic assay system as claimed in claim 6 wherein co-exposing the bioluminogenic substrate to a bioluminescence indicator reaction is performed using a bioluminescence enzyme vector transfected into a biological cell.

9. The bioluminogenic assay system as claimed in claim 6 wherein the bioluminogenic assay system is performed in vivo.

10. The bioluminogenic assay system as claimed in claim 6 wherein the beta-lactamase enzyme is provided within a biological specimen.

11. A bioluminogenic assay system comprising:
a bioluminogenic substrate incorporating a beta-lactam antibiotic, a bioluminescence initiating compound, and an ether bond linking the beta-lactam antibiotic to the bioluminescence initiating compound, the bioluminescence initiating compound being selected from a D-luciferin molecule, a coelenterazine molecule, and their derivatives and analogs;
a beta-lactamase enzyme that catalyzes the release of the bioluminescence initiating compound from the bioluminogenic substrate;
a bioluminescence indicator reaction catalyzed by a bioluminescent enzyme that employs the bioluminescence initiating compound as a substrate; and
an optoelectronic sensor for measuring a light from the bioluminescence indicator reaction as a measure of the activity of the beta-lactamase enzyme.

12. The bioluminogenic assay system as claimed in claim 11 wherein the beta-lactamase enzyme is expressed inside a biological cell from a transfected beta-lactamase vector.

13. The bioluminogenic assay system as claimed in claim 11 wherein the bioluminescence indicator reaction employing the bioluminescence initiating compound is catalyzed by a bioluminescent enzyme expressed inside a biological cell from a transfected bioluminescence enzyme vector.

14. The bioluminogenic assay system as claimed in claim 11 wherein the-bioluminogenic assay system is performed in vivo.

15. The bioluminogenic assay system as claimed in claim 11 wherein the beta-lactamase enzyme is provided within a biological specimen.

16. The bioluminogenic assay system as claimed in claim 11 wherein the beta-lactam antibiotic is a cephalosporin molecule.

17. The bioluminogenic assay system as claimed in claim 16 wherein the bioluminescence indicator reaction is catalyzed by a firefly luciferase enzyme.

18. The bioluminogenic assay system as claimed in claim 16 wherein the bioluminescence indicator reaction is catalyzed by a *Renilla* luciferase enzyme.

* * * * *